United States Patent [19]
Lueck

[11] Patent Number: 5,302,351
[45] Date of Patent: Apr. 12, 1994

[54] LENGTH OF STAIN DOSIMETER

[75] Inventor: Dale E. Lueck, Merritt Island, Fla.

[73] Assignee: The United States of America as represented by the Administrator of the National Aeronautics and Space Administration, Washington, D.C.

[21] Appl. No.: 976,853

[22] Filed: Nov. 16, 1992

[51] Int. Cl.⁵ .................... G01J 1/48; G01N 30/90
[52] U.S. Cl. ........................... 422/87; 422/86; 422/88; 422/89; 436/162
[58] Field of Search .................. 436/162; 422/87, 88, 422/89, 86

[56] References Cited

U.S. PATENT DOCUMENTS

| | | | |
|---|---|---|---|
| 3,985,017 | 10/1976 | Goldsmith | 422/83 |
| 4,023,930 | 5/1977 | Blunck et al. | 436/44 |
| 4,348,358 | 9/1982 | McKee et al. | 422/58 |
| 4,438,205 | 3/1984 | Saint-Leger et al. | 436/162 |
| 4,828,704 | 5/1989 | Yamamoto | 436/162 |
| 4,913,882 | 4/1990 | May et al. | 422/58 |
| 5,116,577 | 5/1992 | Eickeler | 422/88 |
| 5,166,075 | 11/1992 | Fehder | 422/87 |

OTHER PUBLICATIONS

Fisher Scientific Catalog p. 96C.
The Merck Index pp. 355-356.

Primary Examiner—James C. Housel
Assistant Examiner—Rachel Freed
Attorney, Agent, or Firm—William J. Sheehan; Guy M. Miller; John R. Manning

[57] ABSTRACT

Payload customers for the Space Shuttle have recently expressed concerns about the possibility of their payloads at an adjacent pad being contaminated by plume effluents from a shuttle at an active pad as they await launch on an inactive pad. As part of a study to satisfy such concerns a ring of inexpensive dosimeters was deployed around the active pad at the inter-pad distance. However, following a launch, dosimeters cannot be read for several hours after the exposure. As a consequence factors such as different substrates, solvent systems, and possible volatilization of HCl from the badges were studied. This observation led to the length of stain (LOS) dosimeters of this invention. Commercial passive LOS dosimeters are sensitive only to the extent of being capable of sensing 2 ppm to 20 ppm if the exposure is 8 hours. To map and quantitate the HCl generated by Shuttle launches, and in the atmosphere within a radius of 1.5 miles from the active pad, a sensitivity of 2 ppm HCl in the atmospheric gases on an exposure of 5 minutes is required. A passive length of stain dosimeter has been developed having a sensitivity rendering it capable of detecting a gas in a concentration as low as 2 ppm on an exposure of five minutes.

4 Claims, 5 Drawing Sheets

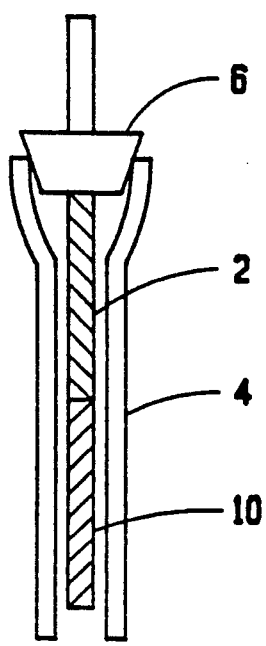
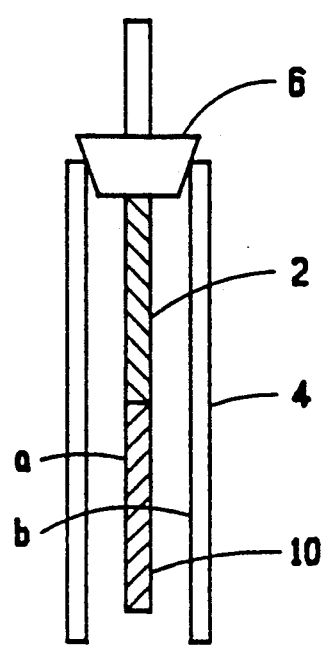
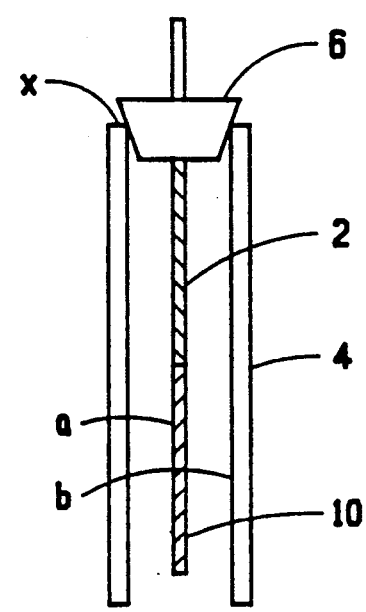
Fig. 1        Fig. 2        Fig. 3
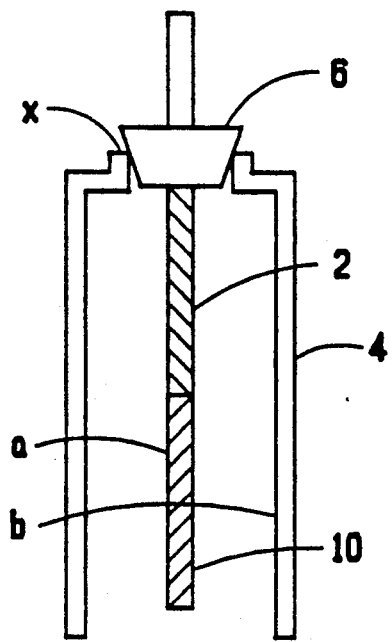
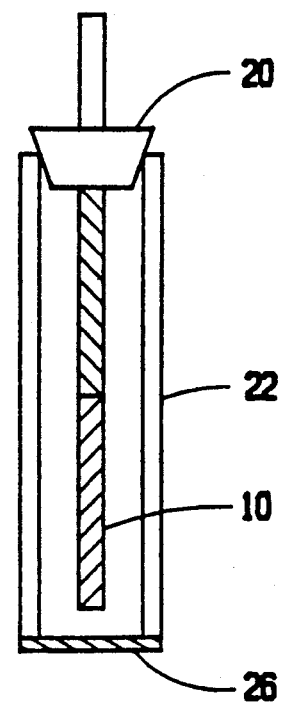
Fig. 4        Fig. 11

LENGTH OF STAIN DOSIMETER

ORIGIN OF THE INVENTION

The invention described herein was made by an employee of the United States Government and may be manufactured and used by or for the Government of the United States of America for Governmental purposes without the payment of any royalties thereon or therefor.

BACKGROUND OF THE INVENTION

This invention, in one of its aspects, pertains to the detection or measurement of hydrogen chloride gas in areas around Space Shuttle launch pads. In another of its aspects the invention relates to a length of stain dosimeter sufficiently sensitive and accurate to measure such gases, even after several hours have elapsed.

Payload customers for the Space Shuttle have recently expressed concerns about the possibility of their payloads at an adjacent pad being contaminated by plume effluents from a shuttle at an active pad as they await launch on an inactive pad. As part of a study to satisfy such concerns a ring of inexpensive dosimeters was deployed around the active pad at the inter-pad distance. Coupled with active measurements of the HCl intrusion through the air handling system on the active pad, it would then be possible to model the expected HCl concentrations at the inactive pad inside the PCR should the plume pass directly over an inactive pad during a future launch.

Initial studies involved the use of paper badge type dosimeters based on modifications of hydrazine-vanillin and bromophenol blue indicators. It was found that rapid fading of the color developed by these systems made their use difficult if not impossible. Following a launch, dosimeters cannot be read for several hours after the exposure. With the date for deployment approaching it was decided to look at the factors affecting fading in such passive dosimeters.

Factors such as different substrates, solvent systems, and possible volatilization of HCl from the badges were studied. Since interaction of the substrate with the dye formulation could be most quickly seen by dropping 100 $\mu l$ of the dye (indicator reagent) test solution onto a horizontally suspended substrate and watching for color changes at the edge of the spreading drop, this method was employed. Many papers were found to be basic or acidic by using acid or base forms of bromophenol blue (BPB) dye. Even "Chromo 1" (a high purity paper used in paper chromatography) and silica gel thin layer chromatography (TLC) plates exhibited rapid fading of the developed color unless very heavy acid exposures were used. Only when Teflon and glass disks were used could light exposure colors be retained. This observation led to the length of stain (LOS) dosimeters of this invention.

Length of stain dosimeters are known in the art, as exemplified by U.S. Pat. Nos. 4,348,358, 4,489,164, 4,904,449, 4,913,882 and 4,963,324. Of these U.S. Pat. No. 4,348,358 is of interest herein. That patent relates to a length of stain (LOS) dosimeter having a detecting strip disposed in a tube with at least one of its sides spaced from the tube along a substantial portion of the length of the strip. The U.S. Pat. No. 4,348,358 is generally directed to porous detecting strips, such as filter paper, blotting paper, felt, cloth and wicks, although incidentally mentioned are nonporous strips of glass rods, glass and plastics. The nonporous strips are thus equated with the porous strips with no obvious advantages. Tube sizes and strip sizes are also mentioned, but no characteristics or teachings are given leading to their application or implementation.

Commercial passive LOS dosimeters are sensitive only to the extent of being capable of sensing 2 ppm to 20 ppm if the exposure is 8 hours. U.S. Pat. No. 4,348,358, which shows 5 ppm to 25 ppm over an 8 hour period is within this commercial sensitivity range.

To map and quantitate the HCl generated by Shuttle launches, and in the atmosphere within a radius of 1.5 miles from the active pad, a sensitivity of 2 ppm HCl in the atmospheric gases on an exposure of 5 minutes is required. Translating these values into ppm minutes (ppm X minutes), the only dosimeters known are those having sensitivities in the range or 2 ppm to 20 ppm over an eight hour period (960 ppm min to 9600 ppm min), whereas the dosimeter required in launch areas must have a sensitivity of 10 ppm min. Such a dosimeter is provided herein.

SUMMARY OF THE INVENTION

By the practice of this invention a passive length of stain dosimeter has been developed having a sensitivity rendering it capable of detecting a gas in a concentration as low as 2 ppm on an exposure of five minutes. This dosimeter includes an outer hollow cylinder having an open end and a closed end, and an inner cylinder disposed within the outer cylinder. The two cylinders are arranged concentrically so that the longitudinal axis of the inner cylinder is also the longitudinal axis of the outer cylinder, and so that the outer wall of the inner cylinder is parallel to the inner wall of the outer cylinder. Means are provided for attaching the inner cylinder to the closed end of the outer cylinder. The inner cylinder is a nonporous glass, plastic or metal cylinder capable of being coated with a thin film. Its outer wall has this thin film thereon, a thin film being one less than 1 mil thick. The thin film is a coating including a reagent which undergoes a color change when contacted by the gas being detected. The sensitivity of the device is a result of this thin film, and a ratio of the area of the end of the outer cylinder (the opening) to the surface area of the thin film. These two parameters govern the sensitivity of the device, with sensitivity increasing when the film thickness is decreased and when the ratio is increased.

DETAILED DESCRIPTION OF THE INVENTION

During the experimental stages of this development when Teflon and glass substrates were used, these substrates appeared to be saturated in areas of minute or light dye or indicator reagent concentration, and did not exhibit any fading. This observation led us to suspect that the porous hydrophilic substrates used in previous dosimeters allowed the transport of unreacted base from the interior of the substrate, causing the surface color developed during exposures to low gas concentrations (light exposures), to be converted from the acid form back to the base form. This would account for the rapid fading we observed in a variety of dosimeters which we tested. The use of nonporous substrate elements such as Teflon filter he dynamic range. Dye coatings on such substrates changed i color with very light exposures, but the exposures could not be distinguished from much heavier doses. These effects led us to explore length of stain type dosimeters.

BRIEF DESCRIPTION OF THE DRAWINGS

The parameters essential to this invention can, perhaps, best be explained in conjunction with diagrammatic and graphic representations of those parameters. Hence reference will be made to the following figures in the drawings.

FIGS. 1 thru 4 illustrate, diagrammatically, four forms of dosimeters of this invention.

FIG. 11 is a LOS dosimeter of the invention with a diffusion barrier.

DETAILED DESCRIPTION OF THE INVENTION

Figure 5:
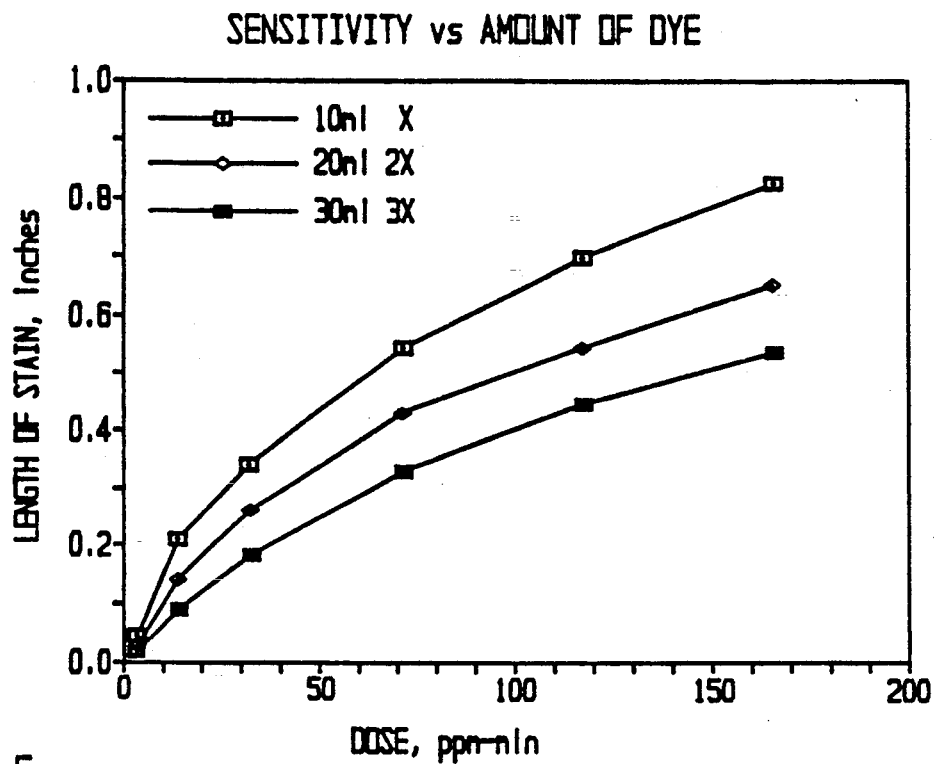
FIG. 5 presents sensitivity curves relating sensitivity to thickness of film on the dosimeter detecting elements.

One embodiment of this invention is a dosimeter 1 of the type illustrated in FIGS. 1 thru 4. A nonporous cylinder 2, such as glass, plastic, or metal, is supported within an outer cylinder 4 by cylinder closure or stopper 6 which closes one end of cylinder 4. The two cylinders 2 and 4 are so disposed that the longitudinal axis of inner cylinder 2 lies on the longitudinal axis of outer cylinder 4. When the outer wall a of inner cylinder 2 is parallel to the inner wall b of outer cylinder 4 there is no unevenness of colorations when a gas contacts a thin film on the outer surface of inner cylinder 2.

Completing the construction of dosimeter 1 is a coating 10 on the outside surface a of the inner cylinder. This coating includes a chemical which undergoes a color change when a gas contacting it contains a compound being detected. In other words the chemical coat on the outer surface of the inner cylinder is responsive to the active chemical, in NASA's use, HCl in the sample gases (atmosphere) contacting that chemical coat. Desirable chemicals for the HCl responsive coating are, then, bromophenol blue (BPB) or an HCl sensitive hydrazine-vanillin dye.

One of the desiderata herein is that a sensitivity of less than 10 ppm min requires a thin film of the detecting reagent or dye on the inner cylinder outer surface. By a "thin film" we mean a film thickness of less than one mil, compared to 2 mil to 5 mil and thicker films applied to dosimeter detecting elements by conventional coating means such as dipping, brushing, and some spray coating techniques. In connection with such thin films Example 1 is given.

EXAMPLE 1

To coat the outer surface of inner cylinders 2 of dosimeters 1 with a thin film of BPB, 0.200 grams of the BPB were dissolved in 100 milliters of methanol. This solution was placed in aspirator painting equipment capable of dispensing an extremely fine spray. Glass cylinders were suspended on a rotating carrier and sprayed by the aspirating apparatus using a high volume (10 liters/min) of air so that the BPB was almost dry when it contacted the glass surface of the inner cylinder. Using this method an evenly distributed thin film was deposited on the outer surface of the cylinders.

To demonstrate the importance of film thickness FIG. 5 is given. This figure is a graph of curves wherein ppm minutes (abscissa) are plotted against the length of stain (ordinate). By curves resulting from the use of different quantities of spray, FIG. 5 shows sensitivity versus amount of HCL indicator or dye, tantamount to film thickness. By spraying different amounts of indicator by the process of Example 1, three quantities of spray, shown in the graph were applied to the inner cylinder outer surface. The result was three film thicknesses, too thin to measure with our equipment, but known to be less than 1 mil thick. Each subsequent inner cylinder was coated with twice as much indicator as the preceding one, and the third had three times ($3\times$) as much as the first. The three curves, $\times$, $2\times$, and $3\times$ show, based on the length of stain, that the dosimeter with thinner film x is more sensitive than dosimeters with $2\times$ and $3\times$ films. And the dosimeter with the $3\times$ film is not as sensitive as the device with the $2\times$ film.

FIGS. 1 thru 4 illustrate larger outer cylinders relative to inner cylinders, with the legend pointing out that they are more sensitive. This is demonstrated by the curves in FIG. 6. The outside circular cross section diameter of the inner cylinder in each case is 0.110 in. The inside diameters of the circular cross sections of the outer cylinders are given in FIG. 6. It can be seen that the device where the inside diameter of the outer cylinder (cross section) was 0.575 in. was more sensitive than the devices with diameters of 0.365 in. or 0.250 in. Due to the accuracy requirements, to be discussed, the 0.250 I.D. unit, shown in FIG. 2, is the "standard" or "STS-42" dosimeter.

The ratio of the inner tube outside diameter (OD) to the outer tube inside diameter (ID) allows the user to modify the dynamic range and sensitivity of the device. Normally this OD : ID ratio should be in the range of 1.5 : 1 to 100 : 1. It will be appreciated, then, (FIG. 5 and FIG. 6) that sensitivity is increased when the film thickness is decreased, and when the OD : ID ratio is increased.

Figure 6:
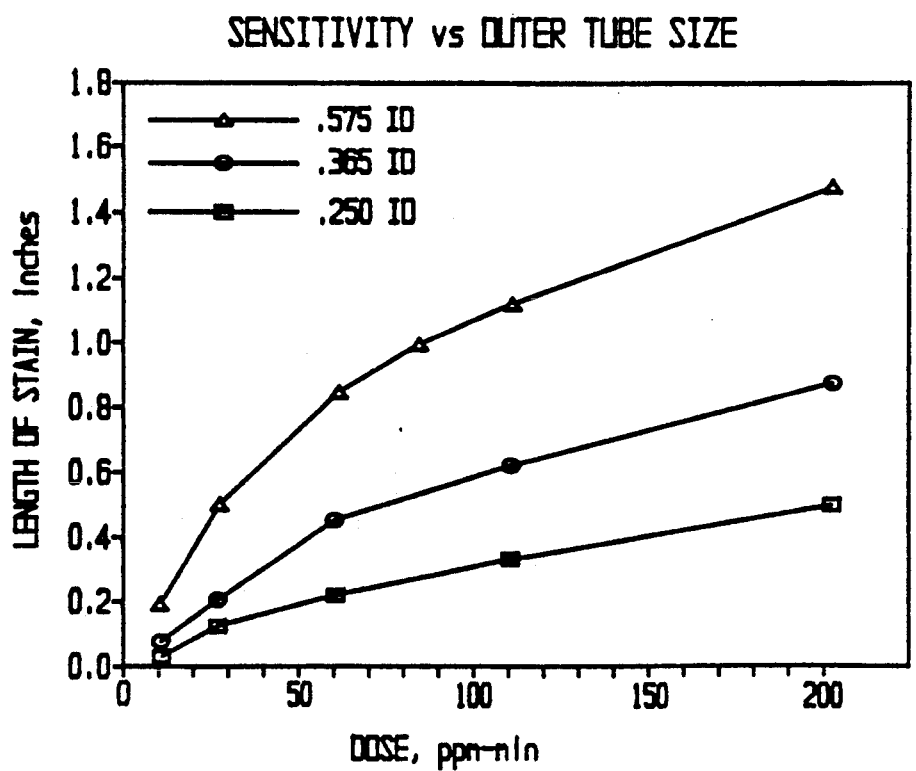
FIG. 6 presents sensitivity curves relating sensitivity to inner cylinder--outer cylinder size ratios.

The two variables demonstrate in FIGS. 5 and 6 do not tell the entire story. There is a trade-off between sensitivity and accuracy. It is to be appreciated that where several variables are involved, as is the case herein, it is impossible to state with precision definite parameters determining a best mode. A sensitive device utilizing some of the variables may not necessarily be the best device. Nevertheless, by following the guidelines set forth herein a device can be produced which is capable of measuring small amounts, 2 ppm, of contaminants in the gas, during short exposures, say less than five minutes. Even so, depending upon circumstances, it may be desirable to sacrifice some sensitivity for accuracy, where accuracy is tantamount to repeatability.

Figure 7:
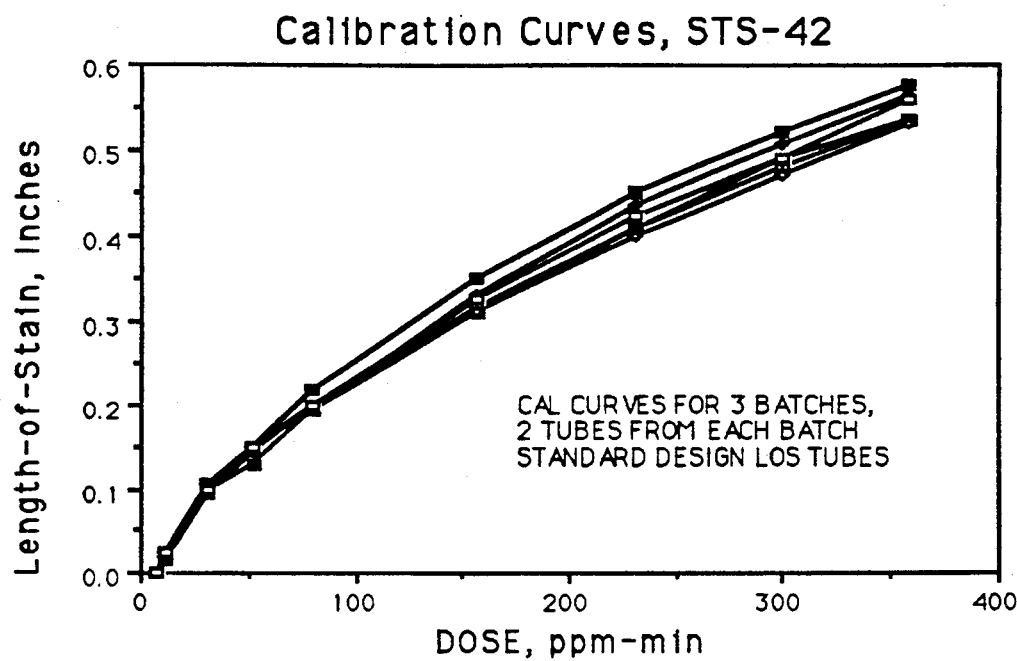
FIG. 7 is a graph of a series of curves showing the accuracy of a standard dosimeter.
Figure 8:
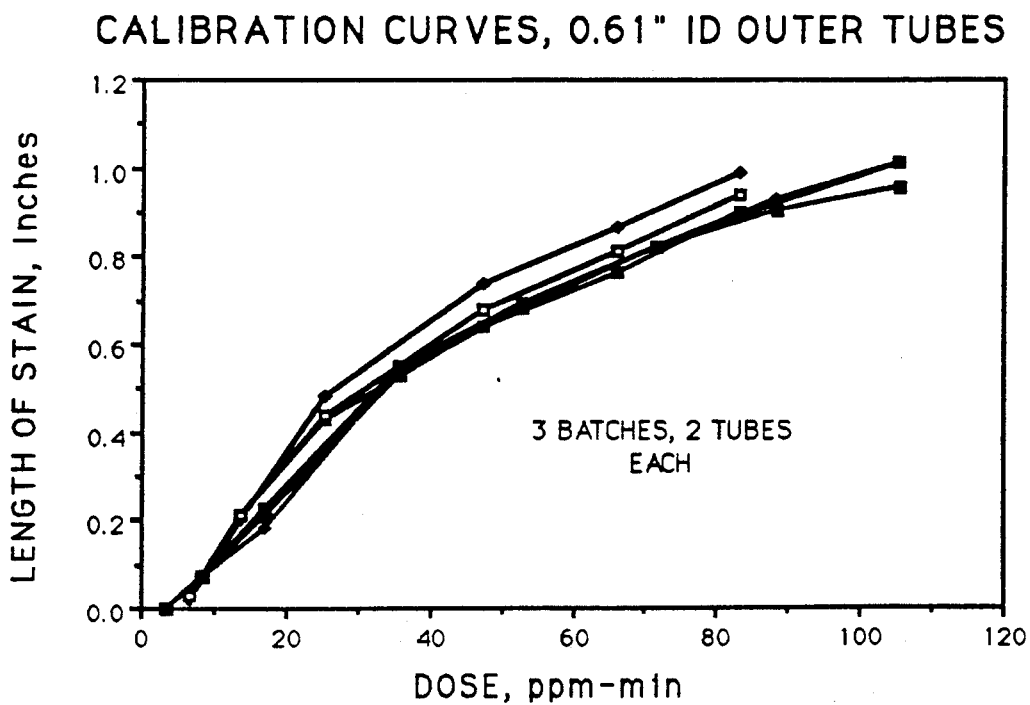
FIG. 8 is a graph similar to FIG. 7 of a series of curves of a different embodiment of the invention.
Figure 9:
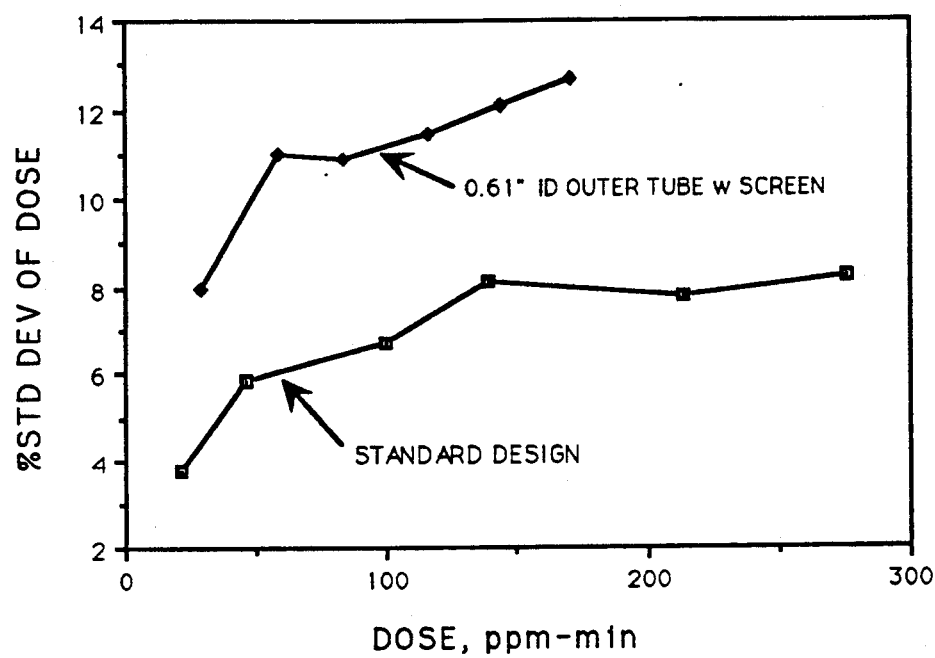
FIG. 9 is an accuracy chart, comparing the standard deviations of the large outer tube and the standard tube designs without a diffusion barrier.
Figure 10:
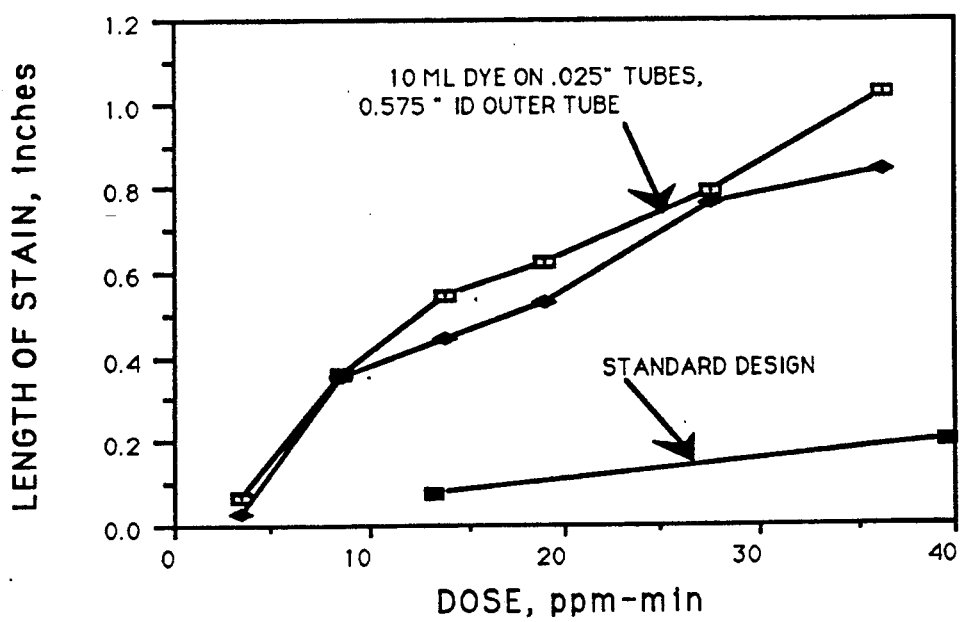
FIG. 10 is a sensitivity comparison showing curves contrasting two dosimeters of the invention.

Relative to accuracy, reference to FIG. 2 is indicated. It will be noted that in terms of the OD : ID ratio, this Standard (StS-42) device is not as sensitive as those in FIG. 3 and FIG. 4. This is shown in FIGS. 7 and 8. FIG. 7 shows sensitivity curves from five runs using the standard device illustrated in FIG. 2. It is apparent that these curves are close together (repeatable) in ppm min as high as over 350 ppm min. Referring now to FIG. 8, it is noted that the six curves begin to diverge at about 10 ppm min if the OD : ID ratio is over 5. This is also illustrated in FIG. 9 which shows a standard deviation, comparing the devices of FIG. 2 (Standard Design) and FIG. 4 (high sensitivity). The Standard Design shows a lower standard deviation (greater accuracy) at all dose levels. The increase in sensitivity with an increase in the OD ID ratio is also shown in FIG. 10. It is to be emphasized, however, that these two can be brought into line if a diffusion barrier, say a porous disc or packing, is placed over the open end of the outer cylinder 4. The diffusion barrier, thus, is another variable to be considered.

The physical arrangement of a suitable diffusion barrier of this invention is shown in FIG. 11. The specific diffusion barrier employed is a porous membrane composed of fluorocarbon fibers, such as Zitex, manufactured by the Chemplast Division of Norton Company. Other inert, porous, and hydrophobic materials will work equally well for hydrogen chloride, with the device sensitivity being affected by the average pore size and the void volume of the diffusion barrier.

Figure 12:
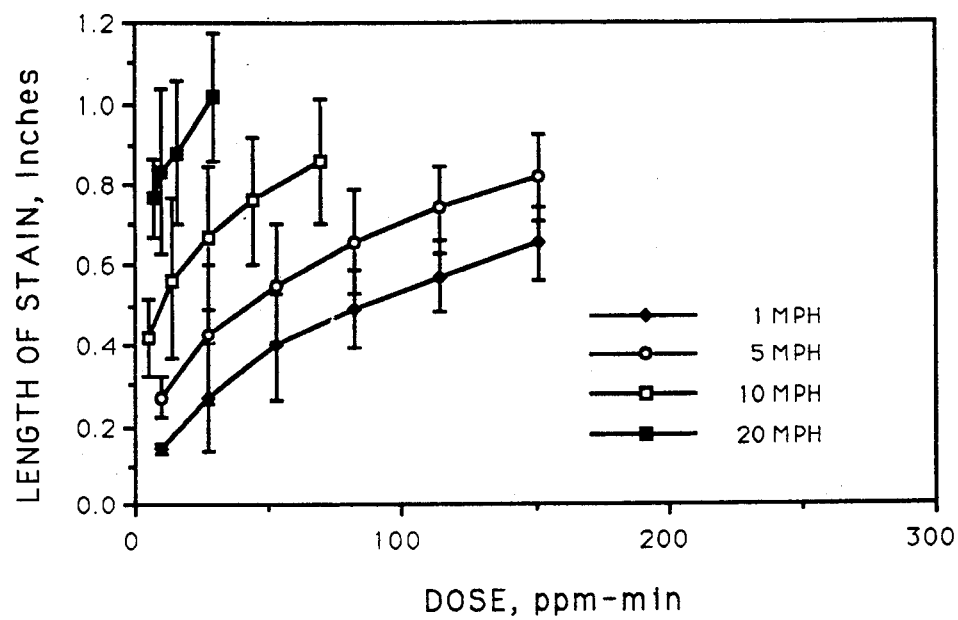
FIG. 12 is a diagram presenting curves showing velocity effects when no diffusion barrier is present.
Figure 13:
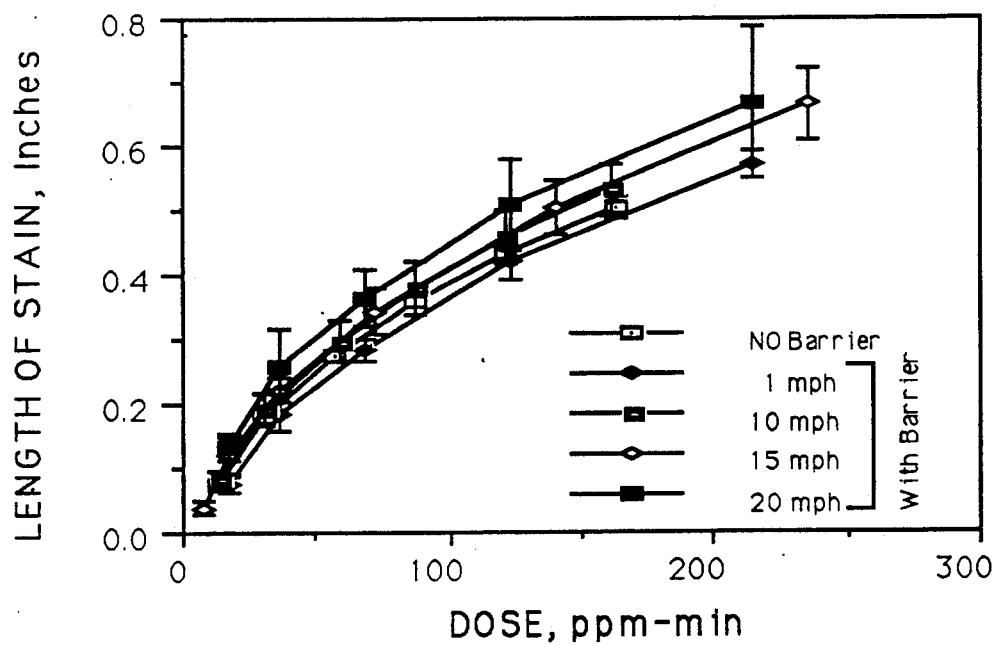
FIG. 13 is similar to FIG. 12 wherein a diffusion barrier is present.

The sample velocity effects without and with the diffusion barrier are shown in FIGS. 12 and 13 respectively. As can be seen, the effects without the barrier are so large as to dominate the quantitation of any hydrogen chloride vapors. With the addition of the barrier, quite reasonable quantitation can occur despite changing sample velocities. It is also to be noted that the addition of the barrier has little effect on the low flow response, as shown by the "no barrier" line in FIG. 13. While known in the art, the use of a diffusion barrier is an important modification within the contemplation of this invention.

It can be seen that by the practice of this invention a dosimeter can be made which is over one hundred times more sensitive than those known in the art.

Having been given the teachings of this invention various ramifications in addition to the variables discussed will occur to those skilled in the art. As an example it has been emphasized that the need herein was for a sensitive dosimeter for HCl detection in an area around a launch pad. It is apparent, however, that the device herein can be utilized for the detection of other undesirable components in gas streams. It is known that the acid and base properties of a number of gases can be used to detect and quantitate their occurrence in gas streams. For this purpose, any number of acid/base indicator dyes can be used. Many other reactions of various gases can also be used for their detection as well. These include a variety of redox, precipitation, and condensation reactions. Any such reaction which produces a color change upon reaction with a sample gas can, in principle, be used with the geometry proposed herein to obtain a more sensitive and reproducible dosimeter. Selection will be within the skill of the art. In addition, a wide range of pretreatments to convert the sought component to a measurable form or to remove potential interferences can be incorporated within the design described herein as part of the diffusion barrier or the reactant layer on the inner tube surface. For certain reactions, the inner wall of the outer tube can also serve as a pre-reaction site. By means known to those skilled in the art all such modifications can be combined with the thin film coaxial detection element described herein.

Selection of the appropriate dye can be made based on available literature. These and other indicator dyes or reagents can thus be applied in thin films, less than 1 mil in thickness, to the outer surface of the inner cylinder by means known in the art, for instance electrodeposition, vapor coating techniques and the like. Further, in order to enhance thin film binding properties, the inner cylinder, especially glass cylinders, can be precoated with a resinous coating material such as an epoxy, acrylic, polyester, polyalcohol, or polyamide.

Metal inner cylinders have been mentioned. These will function the same as glass. However some judgement in their selection is necessary. Thus, a metal will not be selected with a surface which is etched by a component in the gas being detected, or one which has been fabricated with a porous surface. Moreover the inner cylinder need not be a solid. It can be a hollow cylinder. So long as it has a cylindrical outer surface parallel to the inner surface of the outer cylinder for the sake of uniform results its construction is a matter of taste. As an example of another variation of the invention other closure means can be used in the closed end of the outer cylinder in lieu of the stopper 6 shown in the drawings. The outer cylinder end can be rounded off or closed with an orifice therein for insertion of the inner cylinder. The orifice can also be provided with an 0-ring if desired. Further the closed end of the outer cylinder can actually be a flat integral portion of the cylinder and the inner surface can carry a clip for the inner cylinder. The inner cylinder can also be provided with an adhesive removably holding it inside the outer cylinder. These and other ramifications will be obvious to those skilled in the art. Hence they are deemed to be within the scope of this invention.

What is claimed is:

1. A passive length of stain dosimeter having a sensitivity rendering it capable of detecting a gas in a concentration as low as 2 ppm on an exposure of five minutes, the dosimeter comprising an outer hollow cylinder having an inner wall, an open end, and a closed end, an inner cylinder selected from the group consisting of nonporousglass, plastic and metal, having on its outer wall a thin film of a reagent which undergoes a color change when contacted by the gas being detected, means for attaching the inner cylinder to the closed end of the outer cylinder, wherein the inner cylinder is concentrically disposed within the outer cylinder with its outer wall parallel to the inner wall of the outer cylinder and so that its longitudinal axis is also the longitudinal axis of the outer cylinder, wherein the thin film is a film whose maximum thickness is less than 1 mil, and wherein the thickness of the thin film up to its maximum and a ratio of the area of the open end of the outer cylinder to the surface area of the thin film in the range of 1.5:1 to 10:1 govern sensitivity, with sensitivity increasing when the film thickness is decreased and when the ratio is increased.

2. The passive length of stain dosimeter of claim 1 wherein the ratio is 2.2 : 1, and the reagent is bromophenol blue.

3. The passive length of stain dosimeter of claim 1 wherein the ratio is 5:1.

4. The passive length of stain dosimeter of claim 3 wherein a diffusion barrier which covers the open end of the outer cylinder is included.

* * * * *

UNITED STATES PATENT AND TRADEMARK OFFICE
CERTIFICATE OF CORRECTION

PATENT NO. : 5,302,351

DATED : Apr. 12, 1994

INVENTOR(S) : Dale E. Lueck

It is certified that error appears in the above-identified patent and that said Letters Patent is hereby corrected as shown below:

Column 2, line 66, delete "he" and insert therefor --
papers and glass slides reduced the fading rate, but we
lost the --.

Column 2, line 67, delete "i".

Signed and Sealed this

Twenty-seventh Day of September, 1994

Attest:

BRUCE LEHMAN

*Attesting Officer*  *Commissioner of Patents and Trademarks*